United States Patent
Trejbal et al.

(10) Patent No.: US 9,944,748 B2
(45) Date of Patent: Apr. 17, 2018

(54) METHOD OF ISOLATION OF POLYHYDROXYALKANOATES (PHAS) FROM BIOMASS FERMENTED BY MICROORGANISMS PRODUCING POLYHYDROXYALKANOATES (PHAS) AND/OR FROM BIOMASS CONTAINING AT LEAST ONE CROP-PLANT PRODUCING POLYHYDROXYALKANOATES

(71) Applicants: VYSOKA SKOLA CHEMICKO-TECH-NOLOGICKA V PRAZE, Prague (CZ); NAFIGATE CORPORATION, A. S., Prague (CZ)

(72) Inventors: Jiri Trejbal, Kralupy nad Vltavou (CZ); Martin Zapletal, Vsetin (CZ)

(73) Assignees: VYSOKA SKOLA CHEMICKO-TECH-NOLOGICKA V PRAZE, Prague (CZ); NAFIGATE CORPORATION, A.S., Prague (CZ)

( * ) Notice: Subject to any disclaimer, the term of this patent is extended or adjusted under 35 U.S.C. 154(b) by 0 days.

(21) Appl. No.: 15/315,895

(22) PCT Filed: Jun. 2, 2015

(86) PCT No.: PCT/CZ2015/000056
§ 371 (c)(1),
(2) Date: Dec. 2, 2016

(87) PCT Pub. No.: WO2015/185024
PCT Pub. Date: Dec. 10, 2015

(65) Prior Publication Data
US 2017/0107324 A1    Apr. 20, 2017

(30) Foreign Application Priority Data
Jun. 3, 2014 (CZ) .................................. 2014-384

(51) Int. Cl.
*C08G 63/02* (2006.01)
*C08G 63/90* (2006.01)

(52) U.S. Cl.
CPC .................................... *C08G 63/90* (2013.01)

(58) Field of Classification Search
CPC ........................................................ C12P 7/64

USPC ............. 435/41, 67, 89, 101, 122, 134, 136; 528/480
See application file for complete search history.

(56) References Cited

U.S. PATENT DOCUMENTS

| | | | |
|---|---|---|---|
| 4,101,533 A | 7/1978 | Lafferty et al. | |
| 4,140,741 A | 2/1979 | Lafferty et al. | |
| 4,310,684 A | 1/1982 | Vanlautem et al. | |
| 4,324,907 A | 4/1982 | Senior et al. | |
| 4,562,245 A | 12/1985 | Stageman | |
| 4,705,604 A | 11/1987 | Vanlautem et al. | |
| 5,213,976 A | 5/1993 | Blauhut et al. | |
| 2006/0105440 A1 | 5/2006 | Kinoshita et al. | |
| 2007/0161096 A1 | 7/2007 | Mantelatto et al. | |

FOREIGN PATENT DOCUMENTS

| | | |
|---|---|---|
| EP | 0 014 490 | 8/1980 |
| EP | 0 015 123 | 9/1980 |
| EP | 0 036 699 | 9/1981 |
| WO | WO 97/07229 | 2/1997 |
| WO | WO 98/46783 | 10/1998 |
| WO | WO 2009/114464 A1 | 9/2009 |
| WO | WO 2013/016558 | 1/2013 |

OTHER PUBLICATIONS

Search Report, Industrial Patent Office of the Czech Republic, dated Mar. 3, 2015.
PCT Search Report, dated Sep. 29, 2015.

*Primary Examiner* — Terressa Boykin
(74) *Attorney, Agent, or Firm* — Dority & Manning, P.A.

(57) ABSTRACT

A method of isolation of polyhydroxyalkanoates from biomass pre-cleans the biomass in a first extraction process by extracting components of the biomass other than polyhydroxyalkanoates. In a second extraction process, polyhydroxyalkanoates are extracted from a solid phase of the biomass obtained in the first extraction process by adding an extraction agent to pre-cleaned biomass based on chlorinated hydrocarbon, carrying out the extraction for 5 to 90 minutes at a temperature in the range of 20 to 120° C., separating the extract containing the polyhydroxyalkanoates from the extraction solution, and feeding the extract to a circulation loop filled with water having a temperature from 20 to 120° C. or a mixture of water and from up to 20% by weight of the extraction agent based on chlorinated hydrocarbon used for the extraction of polyhydroxyalkanoates, wherein the extraction agent is removed from this extract and polyhydroxyalkanoates precipitate.

14 Claims, No Drawings

METHOD OF ISOLATION OF POLYHYDROXYALKANOATES (PHAS) FROM BIOMASS FERMENTED BY MICROORGANISMS PRODUCING POLYHYDROXYALKANOATES (PHAS) AND/OR FROM BIOMASS CONTAINING AT LEAST ONE CROP-PLANT PRODUCING POLYHYDROXYALKANOATES

TECHNICAL FIELD

The invention relates to a method of isolation of polyhydroxyalkanoates (PHAs) from biomass fermented by microorganisms producing polyhydroxyalkanoates and/or from biomass containing at least one crop-plant producing polyhydroxyalkanoates in which polyhydroxyalkanoates are separated by extraction from the biomass with an extraction agent based on chlorinated hydrocarbon, whereupon an extract is separated from the extraction solution thus obtained and, subsequently, polyhydroxyalkanoates precipitate from the extract.

BACKGROUND ART

Polyhydroxyalkanoates (PHAs) are becoming more and more important, offering a promising alternative to conventional plastics, since they have favourable mechanical properties and, unlike other biopolymers, behave as thermoplastics. Furthermore, they can be recovered from renewable resources, such as biomass—namely either from biomass fermented by microorganisms producing PHAs during their life cycle as their food and energy reserves, or from biomass produced from or containing at least one crop-plant producing PHAs, such as genetically modified maize. Moreover, in the first case by selecting a strain of microorganisms and/or a carbon source for cultivation (saccharides/lipids), it is possible to obtain different compositions of PHAs, and as a result of providing suitable growth conditions for the employed microorganisms, the content of PHAs in their cells can reach up to 90%. In addition, when using the bacteria of the strain *Cupriavidus necator* H16 during the fermentation, it is possible to consume waste edible oils from thermal preparation of food as a carbon source, whose advantage is their low price and commercial availability. The best-known type of PHAs is polyhydroxybutyrate (PHB) and its copolymers containing 3-hydroxyvalerate and 3-hydroxyhexanoate.

Nowadays, there are known several methods of separating PHAs from biomass containing PHAs in which various solvents are used, such as partially halogenated hydrocarbons (see e.g. EP 0015123 and U.S. Pat. No. 4,324,907), carbonates (see e.g. U.S. Pat. No. 4,101,533 and U.S. Pat. No. 4,140,741), higher alcohols and their esters (see e.g. US 2007/0161096, WO 97/07229 and WO 2009/114464) and other substances, such as esters of dicarboxylic and tricarboxylic acids and gamma-butyrolactone (see e.g. U.S. Pat. No. 4,968,611), etc., which extract PHAs from biomass and from which PHAs are subsequently separated in a suitable method. The disadvantage of these processes is the fact that due to the character of the solvents employed they take place at higher temperatures which at the same time cause thermal degradation of the isolated PHA.

From this point of view, the most advantageous solution is using extraction agents based on chlorinated hydrocarbons, since that enables to separate PHA at low temperatures (generally ranging approximately from 100 to 120° C.), at which thermal degradation of PHA does not occur yet (see e.g. U.S. Pat. No. 4,310,684, EP 0014490, U.S. Pat. No. 4,562,245, U.S. Pat. No. 4,705,604 and U.S. Pat. No. 5,213,976). However, during testing these methods, it was found that extraction agents based on chlorinated hydrocarbons extract, apart from PHAs, also other components from the biomass, which during subsequent separation precipitate in water together with PHAs, thus substantially decreasing their final purity. Consequently, the purity reaches approximately 90% at the most (see e.g. the comparative example 1 hereinafter). In addition, in the method according to U.S. Pat. No. 5,213,976, insufficient water turbulence during precipitation leads to the formation of large particles of PHA, which have to be additionally disintegrated.

An alternative method in which the contamination of PHAs with undesired components of the biomass is eliminated is precipitation of PHAs with an organic solvent. However, costs of further disposal of this organic solvent (which is used in considerable excess) are high, and PHAs precipitate in the form of gel having a high moisture content, and so they have to be further dried.

SUMMARY OF THE INVENTION

An aim of the invention is to propose a method of isolation of polyhydroxyalkanoates from biomass fermented by microorganisms producing polyhydroxyalkanoates and/or from biomass containing at least one crop-plant producing polyhydroxyalkanoates, which would lead to their isolation with high purity and, as the case may be, also in the form of smallest possible particles. Additional objects and advantages of the invention will be set forth in part in the following description, or may be obvious from the description, or may be learned through practice of the invention.

The goal of the invention is achieved by a method of isolation of polyhydroxyalkanoates from biomass fermented by microorganisms producing polyhydroxyalkanoates and/or from biomass containing at least one crop-plant producing polyhydroxyalkanoates in which polyhydroxyalkanoates are extracted with an extraction agent based on chlorinated hydrocarbon from the biomass. If fermented, the biomass is first inspissated by isolation from a fermentation medium to a dry matter content of at least 20%. From this extraction solution thus obtained, an extract is separated from which the extraction agent is removed and polyhydroxyalkanoates precipitate. Before the extraction of polyhydroxyalkanoates from the biomass, by means of an extraction agent based on alkyl alcohol having 2 to 4 carbon atoms in the chain, which is added to the biomass in a weight ratio from 1:0.5 to 1:5, preferably from 1:2 to 1:3, components of the biomass other than polyhydroxyalkanoates are extracted. This extraction is carried out for 5 to 90 minutes, preferably for 20 to 40 minutes, at a temperature in the range of 20 to 120° C. After that, the extract containing these components of the biomass is separated from the extraction solution thus obtained by filtration and/or decantation and/or centrifugation. The remainder of the extraction agent is removed from the solid phase by distillation from an aqueous solution or by stripping with water vapour or by drying solid content. From the solid phase thus pre-cleaned, polyhydroxyalkanoates are extracted by means of the extraction agent based on chlorinated hydrocarbon, which is added to it in a weight ratio between 1:5 and 1:20, whereby this extraction operation is carried out for 5 to 90 minutes, preferably for 20 to 40 minutes, at a temperature in the range of 20 to 120° C., whereupon the extract containing polyhydroxyalkanoates is separated from the extraction solution thus obtained by means of filtration and/or decantation and/or centrifugation.

This extract is subsequently fed or continuously fed to a circulation loop filled with water having a temperature from 20 to 120° C., or, as the case may be, by a mixture made from water and from up to 20% by weight of extraction agent based on chlorinated hydrocarbon used for the extraction of polyhydroxyalkanoates, by which means the extraction agent is removed from this extract and polyhydroxyalkanoates precipitate. The purity of the polyhydroxyalkanoates recovered in this manner exceeds 99%, achieving a yield of 97% and more. The particle size of the polyhydroxyalkanoates obtained is then approximately 1 mm.

In order to obtain PHA with a higher degree of purity, the extraction process by means of an extraction agent based on alkyl alcohol having 2 to 4 carbon atoms in the chain may run in more stages, each of which is carried out for 5 to 90 minutes, at a temperature in the range between 20 and 120° C., and before each succeeding stage the solid phase from the preceding stage is concentrated by decantation and/or filtration and/or centrifugation.

Suitable alkyl alcohol extraction agents include ethanol, propanol, isopropyl alcohol, butanol, isobutyl alcohol, tert-butyl alcohol, or a mixture of at least two thereof.

So as to achieve a higher yield of polyhydroxyalkanoates, the extraction process by means of an extraction agent based on chlorinated hydrocarbon can run in more stages, each of which is carried out for 5 to 90 minutes, at a temperature from 20 to 120° C., and before each succeeding stage the solid phase from the preceding stage is concentrated by decantation and/or filtration and/or centrifugation.

Suitable extraction agents based on chlorinated hydrocarbon are dichlormethan, chloroform, tetrachlormethan, dichlorethan, or a mixture of at least two thereof.

From the point of view of reducing the amount of the extraction agent used (both extraction agents based on alkyl alcohol having 2 to 4 carbon atoms in the chain and extraction agents based on the chlorinated hydrocarbons), it is advantageous if the individual stages of the extraction are performed in mutually countercurrent operation, when the extract from each succeeding stage is returned to the preceding stage, the "pure" extraction agent being fed only to the last stage.

If the remainder of the extraction agent based on alkyl alcohol having 2 to 4 carbon atoms is removed from the solid phase by distillation, it is advantageous if the solid phase is first diluted with water in a weight ratio between 1:2 and 1:10, and the process of distillation then takes place in a rectification column at a pressure of 0.1 to 6 bar.

If the remainder of the extraction agent based on alkyl alcohol having 2 to 4 carbon atoms is removed from the solid phase by stripping with water vapour, this process of stripping is carried out in a rectification column at a pressure of 0.1 to 6 bar.

In order to accomplish more intense precipitation of PHA, it is advantageous if the extract containing PHA is before being fed to the circulation loop concentrated by evaporating off the extraction agent to obtain a concentration of polyhydroxyalkanoates of 5 to 10%. The condensation heat obtained during this process can be subsequently used for evaporating off the extraction agent based on chlorinated hydrocarbon in the circulation loop.

SPECIFIC DESCRIPTION

In the method of isolation of polyhydroxyalkanoates (PHAs) from biomass fermented by microorganisms which during their life cycle produce PHAs as their food and energy reserves (e.g. by the bacteria of the strain *Cupriavidus necator* H16, etc.) and/or from biomass containing at least one crop-plant producing PHAs (e.g. genetically modified maize, etc.) according to the invention, before the extraction of PHAs from the biomass, its components that could contaminate PHAs are removed and only after that PHAs are extracted from the biomass thus pre-cleaned into the extraction agent based on chlorinated hydrocarbon The extract containing PHA is afterwards fed, or is being continuously fed to a circulation loop, where the extraction agent is removed and PHAs precipitate.

So as to remove the undesired components of the biomass, an extraction agent based on alkyl alcohol with 2 to 4 carbon atoms in the chain is used, such as ethanol, propanol, isopropyl alcohol, butanol, isobutyl alcohol, tert-butyl alcohol, or a mixture of at least two thereof, which is added to the biomass in a weight ratio of 1:0.5 to 1:5, preferably in a weight ratio of 1:2-1:3. The extraction operation is carried out for 5 to 90 minutes, preferably for 20 to 40 minutes, at a temperature of 20 až 120° C., preferably at a temperature by 5° C. lower than the boiling point of the particular extraction solution—the higher the temperature, the higher the proportion of the extracted components of the biomass and therefore also the resultant purity of PHAs. During this extraction the undesired components which would otherwise be extracted during the extraction of PHAs are extracted into the extraction agent based on alkyl alcohol from the biomass, without PHAs being extracted at the same time and without decreasing its concentration in the biomass. After the extraction is completed, the extract containing the undesired components of the biomass is separated from the extraction solution thus prepared by filtration and/or decantation and/or by centrifugation, and from the solid phase the remainder of the extraction agent employed, constituting a substantial portion of its moisture, is removed. This can be carried out, for example, by diluting the solid phase with water followed by boiling off the extraction agent in a rectification column at a pressure of 0.1 to 6 bar (i.e. by distillation from an aqueous solution), whereby the dilution of the solid phase must be sufficient, i.e. in the range of about 1:2 to 1:10 by weight in order to prevent blocking the rectification column. Surprisingly, it was revealed during the experiments that this procedure has also a positive impact on the speed of the subsequent extraction of PHAs into the extraction agent based on chlorinated hydrocarbon.

Another applicable method of removal of the remainder of the extraction agent from the solid phase is stripping with water vapour in the rectification column at a pressure of 0.1 to 6 bar, or its drying.

The extract separated from the extraction solution constitutes the waste of the method of isolation of PHAs according to the invention. It is advantageous if the extraction agent contained in it is recycled from it, for example, by means of distillation from an aqueous solution. At the same time, with the decrease in the concentration of this extraction agent the extracted components of the biomass precipitate. These can be subsequently separated, for example, by filtration and/or decantation and/or centrifugation.

For the purpose of obtaining PHAs with a higher degree of purity, the extraction using an extraction agent based on alkyl alcohol having 2 to 4 carbon atoms can run in more stages (preferably e.g. in two to five stages, or, in case of need, even more), each of which is carried out for the above-mentioned period of time and at the above-mentioned temperature, whereby before each succeeding stage, the solid phase from the preceding stage is concentrated by filtration and/or decantation and/or centrifugation. The conditions of the individual stages of extraction may be the same, or at least one stage may differ from the others by the temperature and/or duration of the extraction. Preferably, the individual stages are carried out in countercurrent operation, i.e. the extract from each next succeeding stage is fed to the preceding stage, whereby the "pure" extraction agent without the extracted substances is fed only to the last stage. Thus it is possible to achieve the same effect as with individual stages being carried out in a co-current arrangement, but the amount of the extraction agent is considerably reduced.

For the extraction of PHAs from the solid phase thus obtained and pre-cleaned, or from the biomass, extraction agent based on chlorinated hydrocarbon is used, added to it in a weight ratio between 1:5 and 1:20. Owing to the fact that the content of PHAs in the extraction solution has an essential influence on the viscosity of the solution and on the subsequent separation of the extract from the solid phase, it is advantageous to select the ratio of the extraction agent to the solid phase in such a manner that the resultant extraction solution has PHA concentration of 1 to 10%, preferably from 3 to 5%. Also, an important parameter is a content of water in the solid phase, which has influence on the speed of extraction—with a low content of water in the biomass it is difficult to extract PHAs into the extraction agent; on the other hand, a higher content of water in the biomass facilitates the process of extraction of PHAs, and so it is not advisable to distill the water. A favourable content of water is in the range between 40 and 70%. The extraction of PHAs is then carried out for 5 to 90 minutes, preferably for 20 to 40 minutes, at a temperature of 20 to 120° C., preferably, however, by 5° C. lower than is the boiling point of the particular extraction solution.

An extract containing PHA is separated from the extraction solution thus prepared by filtration and/or decantation and/or centrifugation. This extract is fed, or is being continuously fed, to a circulation loop filled with water having a temperature of 20 to 120° C., into which from this extraction phase the extraction agent is isolated and PHAs precipitate. Thus, with time passing, the water in the circulation loop turns into a mixture of water and the extraction agent having a concentration of this extraction agent of up to 20% (whereby it does not yet prevent the precipitation of PHA). The circulation loop is composed of a U-shaped pipeline whose rising passage is led to the side of a liquid separator, and their falling passage is led from the bottom of this separator. The circulation of the liquid in the circulation loop is achieved by the siphon effect caused by partial evaporation of the extraction agent during the contact of the extract with the liquid in the loop. Spray application is taken to the lower portion of the rising passage of the circulation loop. This procedure enables to achieve high turbulence in the circulation loop, whereby the speed of the liquid in its rising passage is from 5 to 10 m/s, which causes the precipitation of PHA in the form of small particles which do not have to be subsequently disintegrated.

Before feeding the extract containing PHAs into the circulation loop it is advantageous if this extract is concentrated to reach the PHA concentration of 5 to 10%. This is achieved, for example, by evaporating off the extraction agent, preferably at an increased pressure (1 to 6 bar, preferably 2 to 4 bar), whereby the condensation heat of the vapour can be further used (see below).

The solid phase separated from the extraction solution constitutes the waste of the method of isolation of PHAs according to the invention. It is advantageous if the remainder of the extraction agent is removed from it, for example, by dilution with water and subsequent boiling off (i.e. by distillation). Preferably, this process can be performed in the rectification column, whereby the dilution of the solid phase with water has to be sufficient, i. e. in a range of 1:2 to 1:10, in order to prevent this column from being blocked. It is thus possible to decrease the content of chlorinated substances in this solid phase to less than 1 ppm. The solid residues that have been boiled off can be then separated by filtration and/or decantation and/or centrifugation.

So as to obtain higher yield of PHAs, the extraction using an extraction agent based on chlorinated hydrocarbon can run in more stages (preferably, for example, from two to five stages, or, in case of need, even more), each of which is carried out for the above-mentioned period of time and at the above-mentioned temperature, whereby before each succeeding stage the solid phase is separated from the extraction solution by filtration and/or decantation and/or centrifugation. The conditions of the individual stages of the extraction can be the same, or at least one stage can differ from the others by the temperature and/or duration of the extraction. Preferably, the individual stages are carried out in a countercurrent operation, i.e. the extract from each succeeding stage is fed to the preceding stage, whereby the "pure" extraction agent without the extracted substances is fed only to the last stage. Thus it is possible to achieve the same effect as if the individual stages were carried out in a cocurrent operation, but the amount of the extraction agent is considerably reduced. Subsequently, the extracts separated in the individual stages of the extraction are mixed together and are fed to the circulation loop.

The benefit of this process is the fact that for evaporating off the extraction agent based on chlorinated hydrocarbon from the extract, it is possible to employ the condensation heat of the vapour of this extraction agent obtained during the concentration of the extract containing PHAs. The heat is fed to the circulation loop through a heat exchanger arranged in its rising passage, which considerably reduces the overall operational costs of the isolation of PHAs. Another variation of a heat source is, for example, a vapour condensate.

PHAs are fed from the circulation loop in the form of suspension, preferably through a centrifugal filter, on which it is possible to achieve a low moisture content of the product—in the range between approximately 10 and 20%. After that, in case of need, the product is further dried.

Before starting the process of isolation of PHAs according to the invention, it is favourable to concentrate the biomass or the fermentation solution obtained by its fermentation to obtain a concentrate having a dry matter content of 20 to 80%, preferably between 40 and 60%. As an advisable method of concentration e.g. decantation is recommended, since it also enables to remove from the biomass waste edible oil which has been used as a source of carbon during the fermentation of the biomass and has not been consumed. Beside that, it is also possible to use filtration and/or centrifugation.

Described hereinafter are two concrete examples of employing the method of isolation of PHAs from biomass fermented by microorganisms producing PHAs according to the invention. However, it is clear from the gist of the matter that if other substances are used (especially extraction agents), or if there are other parameters of individual extractions or stages of extractions or, as the case may be, other techniques used in individual steps mentioned above as well as in the patent claims, the result of the isolation of PHAs will be the same or substantially the same.

EXAMPLE 1

40 kg of 80% aqueous solution of isopropyl alcohol were added to 20 kg of biomass (weight ratio 1:1.6) obtained by centrifugation of a fermentation solution having a dry matter concentration of 45% and PHAs content in the dry matter of 75%, by which means an extraction solution was obtained. The extraction of components of the biomass other than PHAs was then conducted under constant stirring for 30 minutes at a temperature of 75° C. After that this extraction solution was concentrated by centrifugation and another 40 kg of 80% aqueous solution of isopropyl alcohol were added to 19.1 kg of isolated solid phase (weight ratio 1:1.68). The second stage of extraction then took place under the same conditions as the first one, and after its completion the extraction solution was concentrated by centrifugation.

150 kg of water were subsequently added to 18 kg of the solid phase obtained (weight ratio 1:8.3) and the mixture thus prepared was thoroughly stirred. Thereafter the mixture thus obtained was sprayed into the head of a rectification column with structured packing with 10 theoretical plates, to which simultaneously vapour was supplied from the bottom. 16 kg of the solid phase with a dry matter content of 49.5% and the PHAs content in the dry matter of 85.1% were obtained by centrifugation of the column bottom stream from the rectification column, the content of isopropyl alcohol in it being less than 1 ppm.

Subsequently, 120 kg of chloroform were added to 10 kg of the solid phase thus obtained (weight ratio 1:12), by which means an extraction solution was obtained. The extraction of PHAs with chloroform was then carried out under constant stirring for a period of 30 minutes at a temperature of 50° C. After its completion the extraction solution was centrifuged and another 120 kg of chloroform were added to 8.1 kg of the solid phase (weight ratio 1:14.8). The second stage of the extraction of PHAs then took place under the same conditions as the first one. After it had ended, 6.8 kg of the solid phase were obtained by centrifugation of the extraction solution and 0.78 kg of insoluble residues with the PHAs content of 10.8% was further obtained by drying the solid phase at a temperature of 80° C.

The extracts containing PHAs obtained in the individual stages of the extraction were admixed and concentrated to PHAs concentration of 5%. The extract thus obtained was afterwards continuously fed to the lower portion of the circulation loop filled with water pre-heated to 70° C., in the rising passage of which was arranged a vertical heat exchanger malleablized by water having a temperature of 85° C. The speed of the liquid in the falling passage of the circulation loop was 2.5 m/s and in the rising passage of the circulation loop 8 m/s. The mean size of the particles of PHAs precipitated from this liquid in the extract was approximately 1 mm. Subsequently, the resultant suspension was filtered through a nutch filter and the filtered particles of PHAs were dried at a temperature of 80° C., by which means 4.15 kg PHAs with 99.2% purity were obtained (which represents 98% yield).

EXAMPLE 2

25 kg of 90% aqueous solution of ethanol were added to 16 kg of biomass (weight ratio 1:1.4) obtained by centrifugation of a fermentation solution having a dry matter concentration of 47% and PHAs content in the dry matter of 76% by which means an extraction solution was obtained. The extraction of the components of the biomass other than PHAs was then carried out under constant stirring for 30 minutes at a temperature of 65° C. After that this extraction solution was concentrated by centrifugation and another 25 kg of 90% aqueous solution of ethanol were added to 15.3 kg of the isolated solid phase (weight ratio 1:1.47). The second stage of extraction was performed under the same conditions as the first one and after its completion the extraction solution was concentrated by centrifugation.

Subsequently, 150 kg of water were added to 15 kg of the solid phase obtained (weight ratio 1:10) and the mixture thus prepared was thoroughly stirred up. Afterwards this stirred mixture was sprayed to the head of the rectification column with an oriented filling having 10 theoretical floor levels to which simultaneously vapour was supplied from the bottom. 13 kg of the solid phase with a dry matter content of 49.5% and PHAs content in the dry matter of 87.2% were obtained by centrifugation of the residual flow from the rectification column, the content of ethanol in it being less than 1 ppm.

50 kg of tetrachlormethane were then added to 5 kg of the solid phase thus prepared (weight ratio 1:10), by which means an extraction solution was obtained. The extraction of PHA with tetrachlormethane was then carried out under constant stirring for a period of 30 minutes at a temperature of 60° C. After its completion, the extraction solution was centrifuged and another 50 kg of tetrachlormethane were added to 4 kg of the solid phase (weight ratio 1:12.5). The second stage of extraction of PHAs then took place under the same conditions as the first one. After its completion, 3.1 kg of the solid phase were obtained by centrifugation of the extraction solution. Then the solid phase was dried at a temperature of 80° C. and 0.33 kg of insoluble residues were further obtained with PHAs content of 19.9%.

The extracts containing PHAs obtained in the individual stages of extraction were admixed and by evaporating off the tetrachlormethane were concentrated to achieve PHA concentration of 5%. The extract thus obtained was then continuously fed to the lower portion of the circulation loop filled with water pre-heated to 70° C., which had in its rising passage a vertical heat exchanger malleablized by water having a temperature of 85° C. The speed of the liquid in the falling passage of the circulation loop was 2.5 m/s, whereas in the rising passage of the circulation loop it was 8 m/s. The mean size of the particles of PHAs precipitated in this liquid from the extract was approximately 1 mm. The resultant suspense was subsequently filtered through a nutch filter and the filtered particles of PHA were dried at 80° C., by which means 2.14 kg of PHA with the purity of 99.4% were obtained (which represents yield of 97%).

Comparative Example 1—A Method According to U.S. Pat. No. 5,213,976

During the process of testing and verifying the method of isolation of PHAs from biomass according to the U.S. Pat. No. 5,213,976 it was revealed that extraction agents based on chlorinated hydrocarbon are capable of extracting from biomass, apart from PHAs, also other its components which during subsequent precipitation into water precipitate together with PHAs, thus contaminating the PHAs. The purity of PHAs in this case reaches about 92% at the most.

40 kg of chloroform were added to 3.5 kg of the biomass (weight ratio 1:11.4) obtained by centrifugation of a fermentation solution with a dry matter concentration of 47% and with PHAs content in dry matter of 76%, by which means an extraction solution was formed. The extraction of PHAs with chloroform was then carried out under constant stirring for 30 minutes at a temperature of 50° C. Afterwards this extraction solution was concentrated by centrifugation, by which means 1.9 kg of aqueous phase, 4.5 kg of the phase of insoluble residues and 37 kg of extract containing PHAs were obtained. By drying the phase of insoluble residues at 80° C., 0.42 kg of insoluble residues with PHAs content of 32.1% were obtained.

The extract containing PHAs was sprayed through a nozzle to a stirred vessel having a capacity of 200 l with water heated to 80° C., in which PHA precipitated in the form of flakes of the mean size of about 7 mm. The resultant suspension was subsequently filtered through a nutch filter and the filtered particles were dried at a temperature of 80° C., by which means 1.15 kg of PHAs was obtained with the purity of 90.6% (which represents 88% yield).

As the foregoing examples show, the method of isolation of PHAs from biomass according to the invention results in a significantly higher degree of purity of PHAs (approximately by 8 to 9%), with considerably higher yields (approximately by 10%), and at the same time leads to the formation of substantially smaller particles of PHA, which do not need to be further disintegrated (having a diameter seven times smaller).

The invention claimed is:

1. A method of isolation of polyhydroxyalkanoates from biomass, wherein the biomass is either fermented by microorganisms that produce polyhydroxyalkanoates and is first inspissated by isolation from a fermentation medium to a dry matter content of at least 20% or the biomass contains at least one crop-plant that produces polyhydroxyalkanoates, the method comprising:
   pre-cleaning the biomass in a first extraction process by extracting components of the biomass other than polyhydroxyalkanoates by:
      (a) adding to the biomass an extraction agent based on alkyl alcohol having 2 to 4 carbon atoms in the chain in a weight ratio of biomass:extraction agent from 1:0.5 to 1:5;
      (b) carrying out the extraction for 5 to 90 minutes at a temperature in the range of 20 to 120° C.;
      (c) separating the components other than polyhydroxyalkanoates from the extraction solution by any one or combination of filtration, decantation, or centrifugation;
      (d) removing a remainder of the extraction agent from the biomass by distillation from an aqueous solution, stripping with water vapour, or drying;
   in a second extraction process, extracting polyhydroxyalkanoates from a solid phase of the biomass obtained in the first extraction process by:
      (e) adding an extraction agent based on chlorinated hydrocarbon to the biomass in a weight ratio biomass:extraction agent from 1:5 to 1:20;
      (f) carrying out the extraction for 5 to 90 minutes at a temperature in the range of 20 to 120° C.;
      (g) separating the extract containing the polyhydroxyalkanoates from the extraction solution by any one or combination of filtration, decantation, or centrifugation;
      (h) feeding the extract to a circulation loop filled with water having a temperature from 20 to 120° C. or a mixture of water and from up to 20% by weight of the extraction agent based on chlorinated hydrocarbon used for the extraction of polyhydroxyalkanoates, wherein the extraction agent is removed from this extract and polyhydroxyalkanoates precipitate.

2. The method of isolation of polyhydroxyalkanoates from biomass according to the claim 1, wherein the first extraction process runs in at least two stages, wherein each stage is carried out for 5 to 90 minutes at a temperature of 20 to 120° C., and before each succeeding stage the solid phase from the preceding stage is concentrated by any one or combination of decantation, filtration, or centrifugation.

3. The method of isolation of polyhydroxyalkanoates from biomass according to the claim 2, wherein the stages of the first extraction process are carried out in a mutually countercurrent operation.

4. The method of isolation of polyhydroxyalkanoates from biomass according to claim 1, wherein the extraction agent based on alkyl alcohol having 2 to 4 carbon atoms in the chain in the first extraction process is added to the biomass in a weight ratio from 1:2 to 1:3.

5. The method of isolation of polyhydroxyalkanoates from biomass according to claim 1, wherein the first extraction process using an extraction agent based on alkyl alcohol having 2 to 4 carbon atoms in the chain is carried out for 20 to 40 minutes.

6. The method of isolation of polyhydroxyalkanoates from biomass according claim 1, wherein the extraction agent based on alkyl alcohol having 2 to 4 carbon atoms in the chain in the first extraction process is an extraction agent from the group of any one or combination of ethanol, propanol, isopropyl alcohol, butanol, isobutyl alcohol, and tert-butyl alcohol.

7. The method of isolation of polyhydroxyalkanoates from biomass according to claim 1, wherein the second extraction process runs in at least two stages, wherein each stage is carried out for 5 to 90 minutes at a temperature of 20 to 120° C., and before each succeeding stage the solid phase from the preceding stage is concentrated by any one or combination of ecantation, filtration, or centrifugation.

8. The method of isolation of polyhydroxyalkanoates from biomass according to the claim 7, wherein the stages of the second extraction process are carried out in a mutually countercurrent operation.

9. The method of isolation of polyhydroxyalkanoates from biomass according to claim 1, wherein the second extraction process using an extraction agent based on chlorinated hydrocarbon is carried out for 20 to 40 minutes.

10. The method of isolation of polyhydroxyalkanoates from biomass according to claim 1, wherein the extraction agent based on chlorinated hydrocarbon in the second extraction process is an extraction agent from the group of any one or combination of dichlormethan, chloroform, tetrachlormethan, or dichlorethan.

11. The method of isolation of polyhydroxyalkanoates from biomass according to claim 1, wherein the solid phase of the biomass in the second extraction process is diluted with water before distillation of the extraction agent in a ratio of 1:2 to 1:10, and distillation from this aqueous solution is performed in a rectification column at a pressure of 0.1 to 6 bar.

12. The method of isolation of polyhydroxyalkanoates from biomass according to claim 1, wherein stripping with water vapour to remove the extraction agent in step (d) is carried out in a rectification column at a pressure 0.1 to 6 bar.

13. The method of isolation of polyhydroxyalkanoates from biomass according to claim 1, wherein the extract containing polyhydroxyalkanoates is concentrated by evaporating off the extraction agent to reach a concentration of polyhydroxyalkanoates 5 to 10% prior to being fed into the circulation loop.

14. The method of isolation of polyhydroxyalkanoates from biomass according to the claim 13, wherein for evaporating off the extraction agent based on chlorinated hydrocarbon in the circulation loop, condensation heat of vapour of the extraction agent obtained during the concentration of the extract containing polyhydroxyalkanoates is utilized.

* * * * *